US011779711B1

(12) United States Patent
Yang (10) Patent No.: US 11,779,711 B1
(45) Date of Patent: Oct. 10, 2023

(54) ATOMIZER WITH INTELLIGENT CONTROL DIGITAL DISPLAY FUNCTION

(71) Applicant: Shenzhen Haige Cross-border Technology Co., Ltd., Shenzhen (CN)

(72) Inventor: Yunhang Yang, Shenzhen (CN)

(73) Assignee: SHENZHEN HAIGE CROSS-BORDER TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/185,396

(22) Filed: Mar. 17, 2023

Related U.S. Application Data (63) Continuation-in-part of application No. 17/902,260, filed on Sep. 2, 2022, now abandoned.

(51) Int. Cl.
    *A61M 11/02* (2006.01)
(52) U.S. Cl.
    CPC ....... *A61M 11/02* (2013.01); *A61M 2205/502* (2013.01)
(58) Field of Classification Search
    CPC ... A61M 11/02; A61M 16/0063; A61M 15/00
    See application file for complete search history.

(56) References Cited

U.S. PATENT DOCUMENTS

| D527,098 S * | 8/2006 | Cheng | A61M 16/0009 |
| | | | D24/110 |
| 2008/0190417 A1* | 8/2008 | Abate | A61M 11/02 |
| | | | 128/200.14 |
| 2009/0167698 A1* | 7/2009 | Altas | B01D 53/047 |
| | | | 345/173 |
| 2020/0073513 A1* | 3/2020 | Ballan | G06F 3/039 |
| 2021/0187223 A1* | 6/2021 | Sing | A61M 16/0009 |

* cited by examiner

*Primary Examiner* — Margaret M Luarca
(74) *Attorney, Agent, or Firm* — Andrew C. Cheng (57) ABSTRACT

An atomizer with an intelligent control digital display function, including a housing, a control panel and a compressor; the housing is provided with an inlet member and an outlet member; the control panel and the compressor are both arranged in the housing, the compressor is electrically connected with the control panel, the control panel is an intelligent control panel, the control panel has a digital display screen for displaying the working state of the atomizer, and the housing is provided with a cooling grille, and the compressor has an output shaft, and a cooling fan is arranged on the output shaft, the cooling fan is facing the cooling grille. By designing the control panel as an intelligent control panel, the control panel has a digital display screen for displaying the working state of the atomizer, so as to realize the digital display function and bring convenience to use.

20 Claims, 7 Drawing Sheets

ATOMIZER WITH INTELLIGENT CONTROL DIGITAL DISPLAY FUNCTION

CROSS-REFERENCE TO RELATED APPLICATIONS

This application is a continuation-in-part of application Ser. No. 17/902,260 filed on Sep. 2, 2022, the content of which is incorporated herein by reference.

TECHNICAL FIELD

The present application relates to the technology in the field of atomizers, in particular to an atomizer with an intelligent control digital display function.

BACKGROUND

The atomizer is mainly used to treat various upper and lower respiratory diseases, such as colds, fever, cough, asthma, sore throat, pharyngitis, rhinitis, bronchitis, pneumoconiosis and other diseases that occur in the trachea, bronchi, alveoli, and chest. Aerosol inhalation therapy is an important and effective treatment method in the treatment of respiratory diseases. The liquid medicine is atomized into tiny particles by the atomizing inhaler, and the medicine enters the respiratory tract and lungs by breathing inhalation, so as to achieve the purpose of painless, rapid and effective treatment.

Compressed air atomizer is a kind of atomizer, which is also called jet atomization. According to the principle of Venturi injection, compressed air is used to form a high-speed airflow through a small nozzle. The generated negative pressure drives the liquid or other fluids to be sprayed onto the barrier together, and splashes around under the high-speed impact, so that the droplets become mist-like particles and are ejected from the air outlet.

The current air compression atomizer generally does not have a digital display function, which brings inconvenience to use, and has poor heat dissipation effect and short product life. Therefore, it is necessary to improve the current air compression atomizer.

SUMMARY OF THE APPLICATION

In one aspect, the present application provides an atomizer with an intelligent control digital display function which includes a housing, the housing being provided with an inlet member and an outlet member; a control panel arranged in the housing; and a compressor arranged in the housing and electrically connected with the control panel. The compressor includes an input end communicated with the inlet member and an output end communicated with the outlet member. The control panel is an intelligent control panel which includes a digital display screen for displaying working state of the atomizer and a touch switch. A front end of the housing is provided with an opening, the opening is covered with a decorative panel, the outlet member extends through the opening and the decorative panel, the decorative panel faces the control panel with a gap formed therebetween, and the digital display screen and the touch switch are disposed in the gap and visible from outside of the housing through the opening and the decorative panel.

DETAILED DESCRIPTION

In the description of the present application, it should be noted that unless otherwise clearly specified and limited, the terms "installation", and "connection" should be understood in a broad sense, for example, it can be a fixed connection or a detachable connection, or integrally connected; it can be a mechanical connection or an electrical connection; it can be directly connected, or indirectly connected through an intermediate medium, and it can be the internal communication between two components. For those skilled in the art, the specific meaning of the above-mentioned terms in the present application can be understood according to the specific circumstances.

Referring to FIG. 1 to FIG. 6, an atomizer according to an embodiment of the present application includes a housing 10, a control panel 20 partially arranged in the housing 10, and a compressor 30 arranged in the housing 10. The compressor 30 is electrically connected with the control panel 20.

Figure 7:
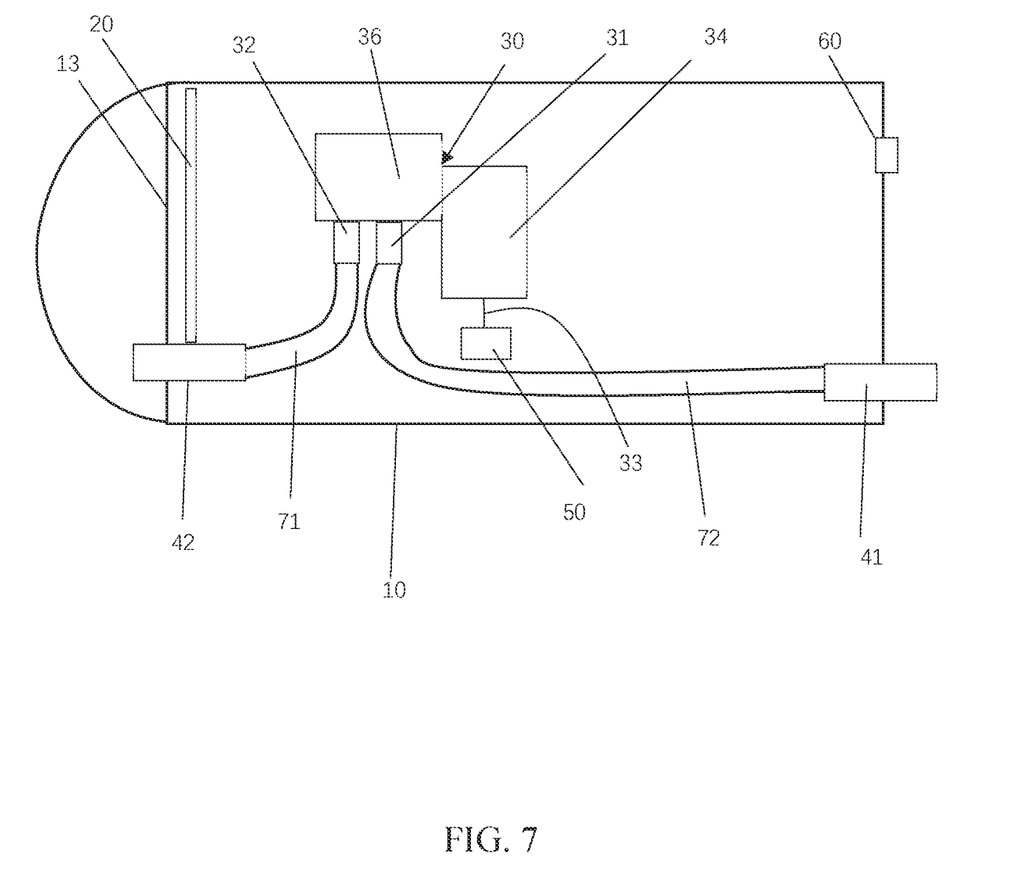
FIG. 7 illustrates an atomizer according to another embodiment of the present application.

The housing 10 is provided with an inlet member 41 and an outlet member 42. The compressor 30 includes an input end 31 in communication with the inlet member 41 and an output end 32 in communication with the outlet member 42. The input end 31 of the compressor 30 may be connected to the inlet member 41 via a connection pipe 71 (FIG. 7). The output end 32 of the compressor 30 may be connected to the outlet member 42 via a connection pipe 72 (FIG. 7). The pipes 71/72 may be soft pipes and made of rubber or the like. The pipes 71/72 may be rigid pipes. In one embodiment, the outlet member 42 and the inlet member 41 are respectively arranged at front and rear ends of the housing 10. The gas-liquid mixture can be directed in the housing 10 from the rear end of the housing 10, and the atomized gas-liquid mixture can be directed out of the housing 10 from the front end of the housing 10.

The axis of the outlet member 42 and the inlet member 41 are substantially parallel with the lengthwise direction of the housing 10, the axis of the input end 31 and the output end 32 of the compressor 30 are also substantially parallel with the lengthwise direction of the housing 10. In one embodiment, when the pipes 71/72 are rigid pipes, the path for directing the gas-liquid mixture and the atomized gas-liquid mixture is substantially parallel with the lengthwise direction of the housing 10, or an angle is defined between the path and the lengthwise direction of the housing 10, and the angle is about 1-15° (in detail, the angle is 1°, 2°, 3°, 4°, 5°, 6°, 7°, 8°, 9°, 10°, 11°, 12°, 13°, 14°, or 15°). The path may be defined as a straight path substantially parallel with the lengthwise direction of the housing 10, or defined as several straight sub paths connected with each other substantially parallel with the lengthwise direction of the housing 10, to improve a transmitting efficiency. The path may be defined as at least one straight path slant to the lengthwise direction of the housing 10, and an angle of about 1-15° is defined between the at least one path and the lengthwise direction of the housing 10. In another embodiment, the pipes 71/72 are flexible, and path includes curved parts and straight parts. The outlet member 42, the inlet member 41, the input end 31, the output end 32, and the pipes 71/72 are all arranged at a side of the compressor 30 away from the fan 50, to reduce a thickness or a height of the housing 10. In this way, the atomizer has a small and compact structure. The outlet member 42 is also arranged at a side of the digital display screen 21 away from the touch switch.

The axis of the input end 31 and the output end 32 of the compressor 30 are perpendicular to the height direction of the housing 10. That is, orientations of the input end 31 and output end 32 of the compressor 30 are perpendicular to the height direction of housing 10, which facilitates to reduce the height of the housing 10. In this embodiment, the input end 31 of the compressor 30 faces the front end of the housing 10, and the output end 32 of the compressor 30 faces the rear end of the housing 10. The axis of the input end 31 is parallel with that of the inlet member 41, the axis of the input end 31 is preferably at least overlapped with that of the inlet member 41; and the axis of the output end 32 is parallel with that of the outlet member 42, the axis of the output end 32 is preferably at least overlapped with that of the outlet member 42. When the connection pipe 71 is a rigid pipe, the axis of the connection pipe 71 is parallel with that of the inlet member 41 or the input end 31, the axis of the connection pipe 71 is preferably at least overlapped with that of the inlet member 41 or the input end 31, or an angle of about 1-15° is defined between the connection pipe 71 and the inlet member 41 or between the connection pipe 71 and the input end 31. When the pipe 72 is a rigid pipe, the axis of the connection pipe 72 is parallel with that of the outlet member 42 or the output end 32, the axis of the connection pipe 72 is preferably at least overlapped with that of the outlet member 42 or the output end 32, or an angle of about 1-15° is defined between the connection pipe 72 and the outlet member 42 or between the connection pipe 72 and the output end 32. In this way, the path for directing the gas-liquid mixture and the atomized gas-liquid mixture is designed to be short, and the atomizer in consequence has a small and compact structure and a high working efficiency.

Preferably, a front end of the housing 10 is provided with an opening 104, and the opening 104 is covered with a decorative panel 13. The outlet member 42 extends through the opening 104 and the decorative panel 13. Specifically, the decorative panel 13 defines a through hole 132 and the outlet member 42 extends through the opening 104 and the through hole 132 sequentially. In some embodiments, the decorative panel 13 is translucent and is made of PMMA (polymethyl methacrylate).

In some embodiments, the housing 10 includes a lower housing 11 and an upper housing 12, and the upper housing 11 and the lower housing 12 are engaged with each other to form an accommodating cavity 102 therebetween. The control panel 20 and the compressor 30 are arranged in the accommodating cavity 102. The outlet member 42 and the inlet member 41 are both arranged at the upper housing 12. The opening 104 is defined in the upper housing 12.

Specifically, the upper housing 12 includes a top wall 122 and a circumferential wall extending from the periphery of the top wall 122 toward the lower housing 11. The bottom of the circumferential wall is connected to the periphery of the lower housing 11. In some embodiments, the circumferential wall of the upper housing 12 has a rectangle cross section and includes a front wall 124, a rear wall 126 and a pair of side walls 128 connected between the front wall 124 and the rear wall 126 respectively. The rear wall 126 defines a through hole for exposing the inlet member 41.

Figure 1:
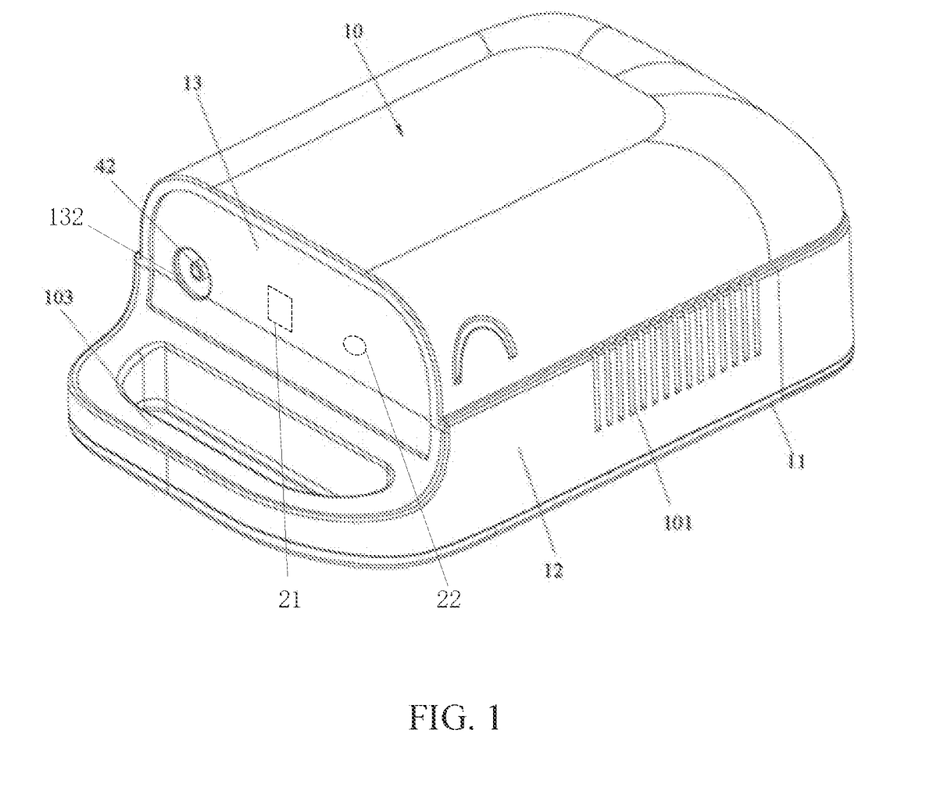
FIG. 1 is the assembled perspective schematic diagram of the preferred embodiment of the present application.
Figure 2:
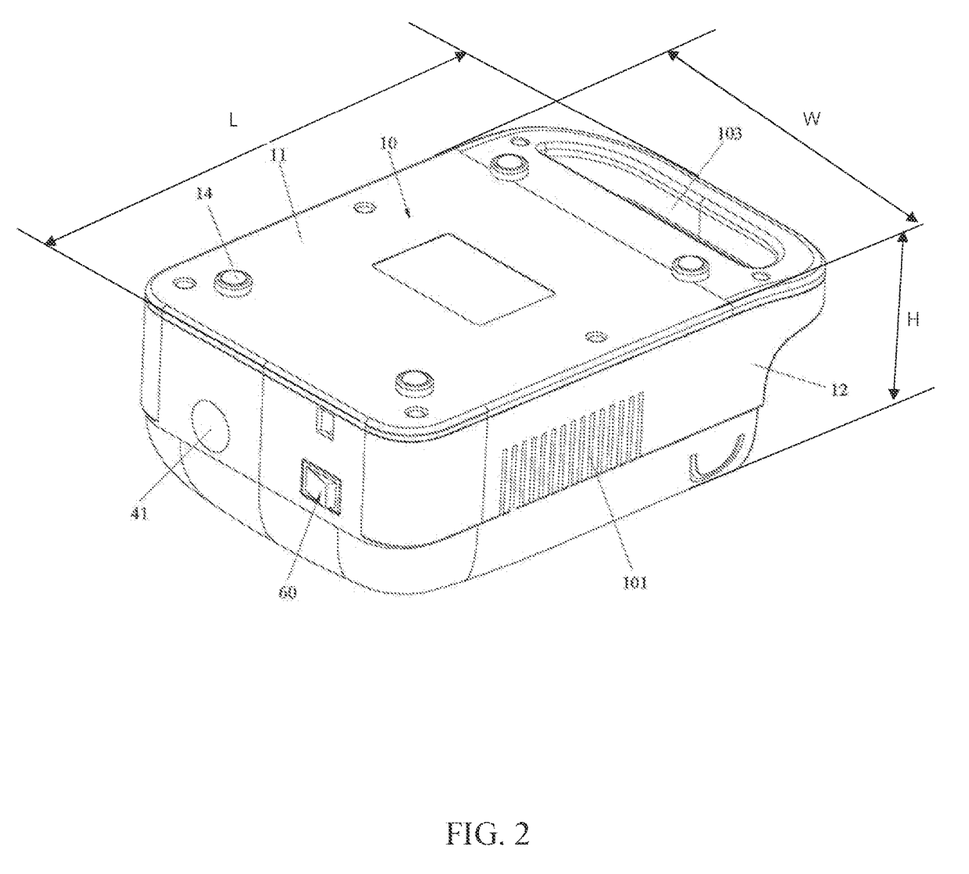
FIG. 2 is the assembled perspective schematic diagram of the preferred embodiment of the present application from another angle.
Figure 3:
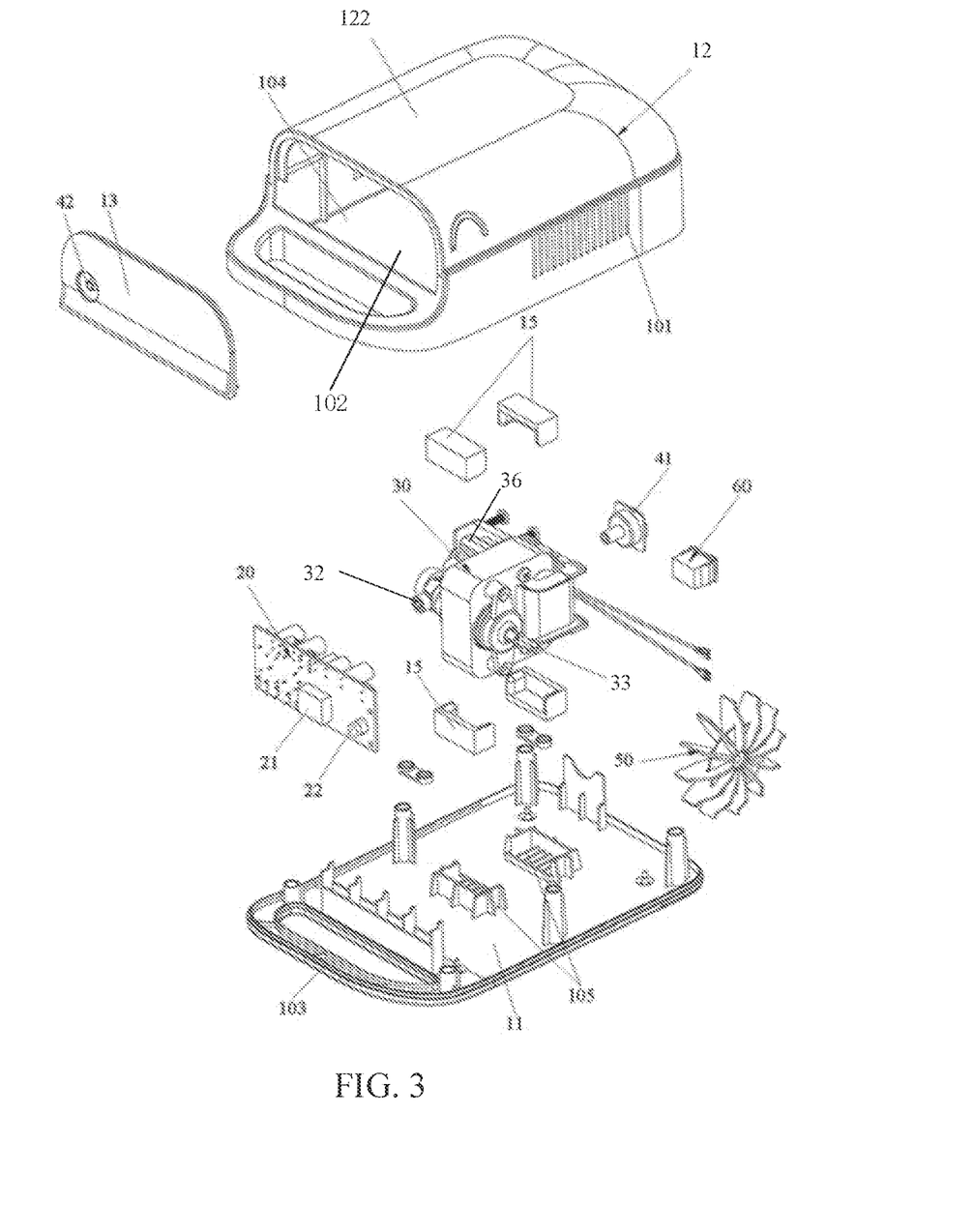
FIG. 3 is an exploded view of the preferred embodiment of the application.
Figure 4:
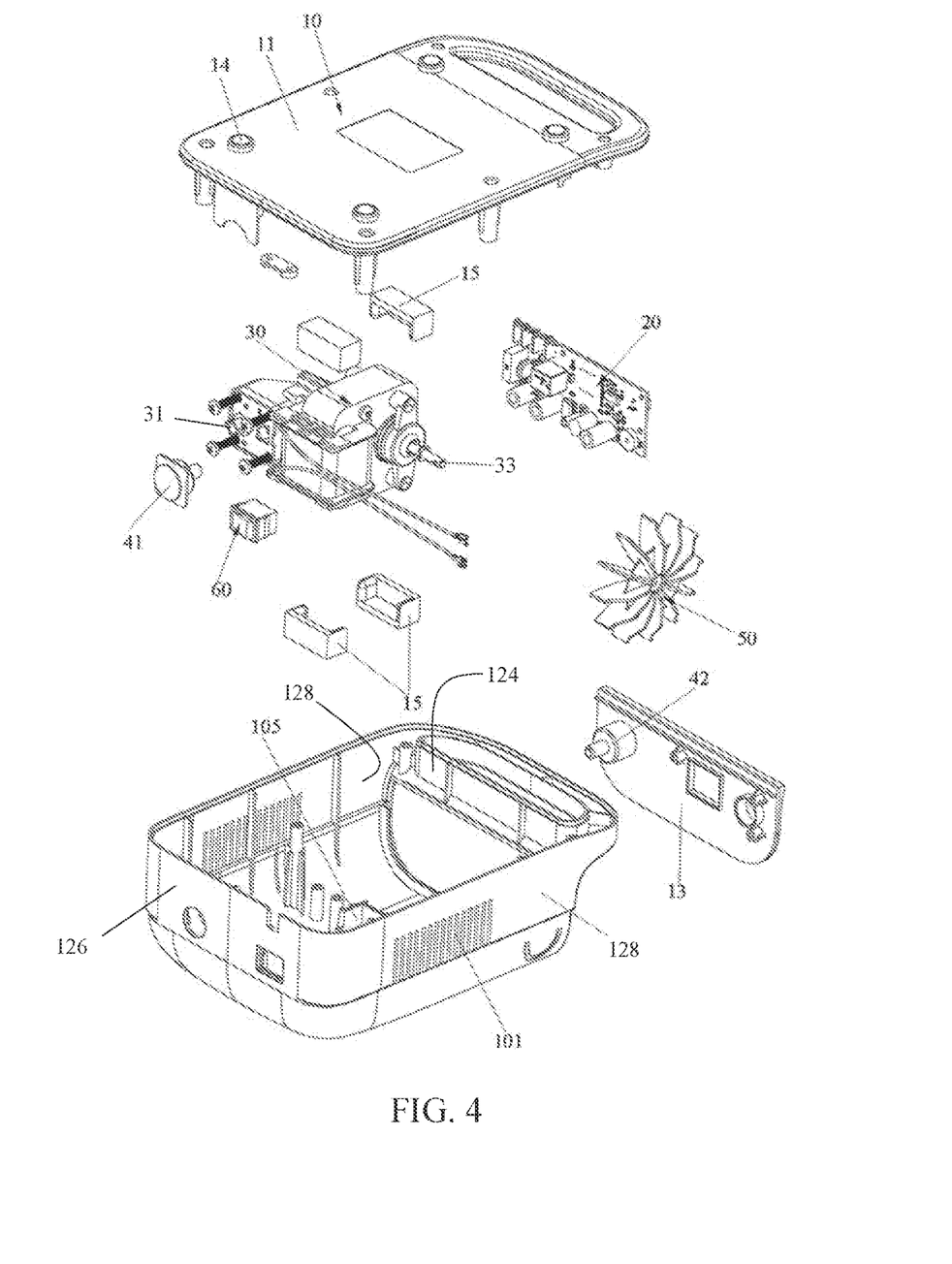
FIG. 4 is an exploded view of the preferred embodiment of the present application from another angle.
Figure 5:
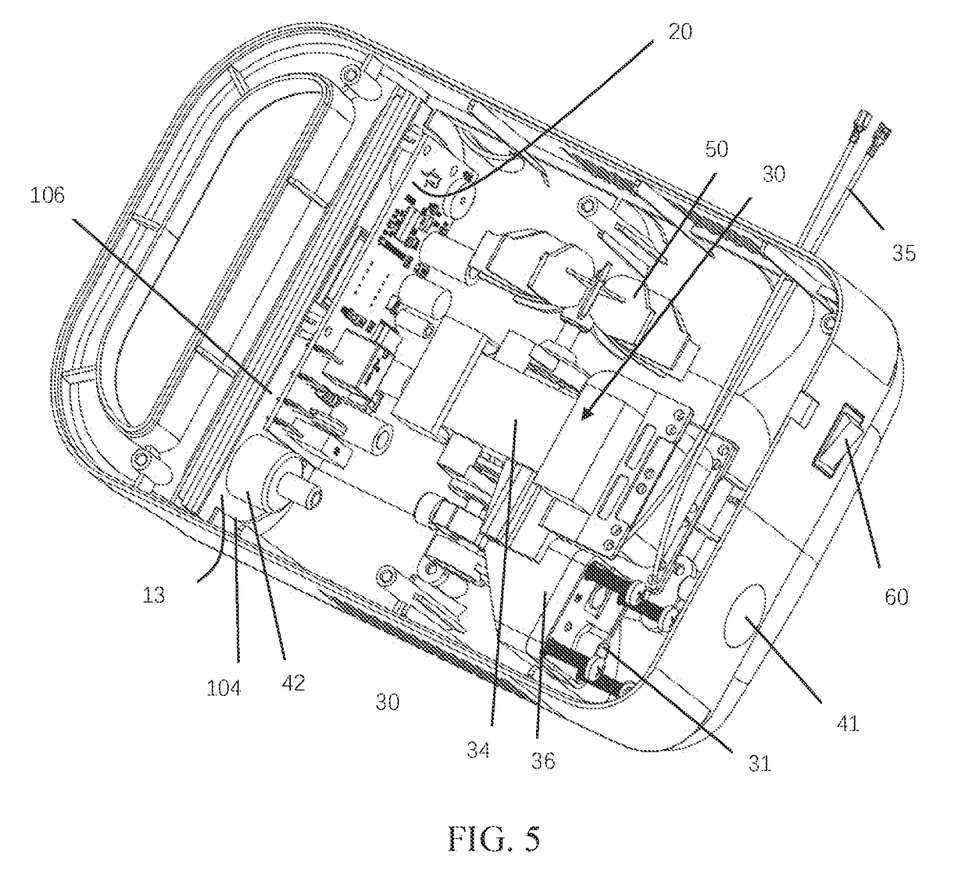
FIG. 5 illustrates the atomizer in another aspect in which the lower housing is removed for facilitating showing the components inside the housing.
Figure 6:
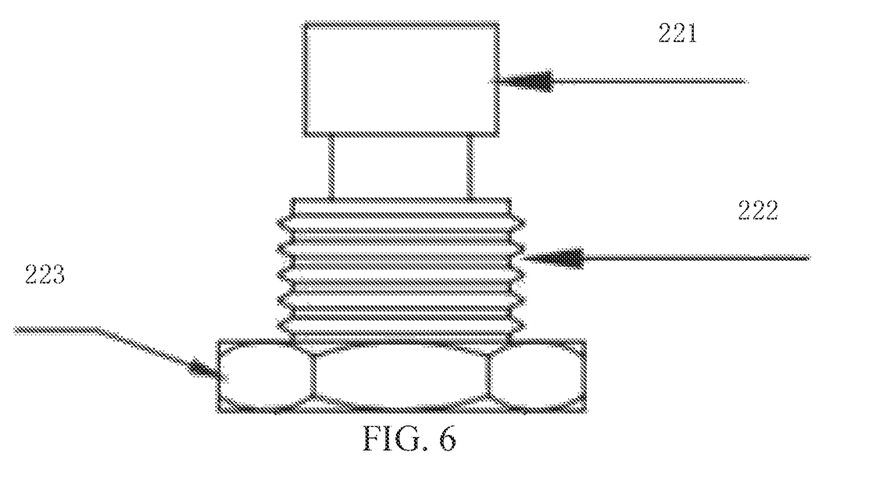
FIG. 6 illustrates a cross sectional diagram of a part of the touch switch.

Referring to FIG. 5, the opening 104 is defined through the front wall 124 of the upper housing 12. The opening 104 is covered by the decorative panel 13. The decorative panel 13 has a shape matching with that of the opening 104. Preferably, the opening 104 and the decorative panel 13 both have a D shape. The control panel 20 is parallel with the decorative panel 13. Both the control panel 20 and the decorative panel 13 are parallel with the height direction of the housing 10 and perpendicular to the lengthwise direction of the housing 10. The control panel 20 and the decorative panel 13 are located at opposite sides of the opening 104. Specifically, the control panel 13 is located inside of the opening 104, and the decorative panel 13 is located outside of the opening 104. The control panel 20 is spaced from the decorative panel 13 with a gap 106 formed therebetween. The control panel 20 includes an outer surface facing the decorative panel 13 and an inner surface facing the compressor 30.

The control panel 20 is an intelligent control panel which includes a digital display screen 21 for displaying the working state of the atomizer and a touch switch 22. The digital display screen 21 and the touch switch 22 both are mounted at the outer surface of the control panel 20 and face the decorative panel 13. The digital display screen 21 and the touch switch 22 are disposed in the gap 106 between the control panel 20 and the decorative panel 13 and are visible from outside the housing 10 through the opening 104 and the decorative panel 13. A thickness of the digital display screen 21 matches with a size of the gap 106, and a height of the touch switch 22 matches with a size of the gap 106, outer surfaces of the digital display screen 21 and the touch switch 22 may be flush with an outer surface of the decorative panel 13 due to the existence of the gap 106. The control panel 20 has an area less than that of the opening 104 to allow the outlet member 42 to pass through the opening 104 and enter inside of the housing 10. Specifically, the control panel 20 has a size along the width direction of the housing 10 less than the size of the opening 104 along the width direction of the housing 10. In another embodiment, the digital display screen 21 and the touch switch 22 are contacted with the inner surface of the decorative panel 13 or arranged to be adjacent to the inner surface of the decorative panel 13. User can touch or press a portion of the decorative panel 13 corresponding to the touch switch 22 to operate.

Preferably, the touch switch 22 is a capacitive touch switch which includes a touch portion 221, a spiral spring 222 with an axis perpendicular to the decorative panel 13 and the control panel 20, and a connecting portion 223 electrically connected with the control panel 20. The spiral spring 222 may be an air spring, or a coil spring. The spiral spring 222 is made of electrically conductive material. When a finger of a user touches a portion of the decorative panel 13 corresponding to the touch switch 22, a capacitor is generated between the finger and the touch switch 22. As a result, a control signal is generated by the control panel 20 to control the compressor 30.

Preferably, the atomizer is portable. The front end of the housing 10 is provided with a handle 103 for easy carrying. Preferably, the handle 103 is C-shaped and extends forwardly from the front end of the housing 10. Specifically, the handle 103 includes two parts extending forwardly from the front ends of the upper housing 12 and the lower housing 11 respectively. Preferably, the two parts of the handle 103 are integrally formed with the upper housing 12 and the lower housing 11 respectively. The upper housing 12 and the lower housing 11 are assembled together, which results in the two parts of the handle 103 being assembled together. The opening 104 is arranged between the handle 103 and the compressor 30, the decorative panel 13, the digital display screen 21 and the touch switch 22 are also arranged between the handle 103 and the compressor 30 as the decorative panel 13, the digital display screen 21 and the touch switch 22 are received in the opening 104. The handle 103 is arranged below the opening 104, the decorative panel 13, the digital display screen 21 and the touch switch 22, so that the handle 103 may not interfere with the digital display screen 21 and the touch switch 22.

In some embodiments, the upper housing 12 is provided with at least one cooling grille 101. The compressor 30 further includes an output shaft 33, and a cooling fan 50 is arranged on the output shaft 33 and is rotatable with the output shaft 33. Preferably, the cooling fan 50 is an axial fan. The axis of the axial fan is perpendicular to the side walls 128. Preferably, a pair of cooling grilles 101 is located on the two side walls 128 of the upper housing 12 respectively and the cooling fan 50 faces one of the cooling grilles 10. The cooling grilles 101 are arranged on two sides of the compressor 30, to improve the heat dissipation efficiency. The length direction of grooves of the cooling grille 101 is substantially parallel with the path for directing the air and the atomized gas. In operation, the cooling fan 50 draws air into the housing 10 from one of the cooling grilles 101 to cool the compressor 30 and forces the air out of the housing via the other of the cooling grilles 10. The cooling grilles 101 are disposed at the side walls 128, which facilitates to reduce the height of the housing 10.

The compressor 30 includes a pair of power lines 35 configured to be connected to a power source. The power lines 35 extend through a side wall 128 of the upper housing 12 to outside the housing 10. Alternatively, the power lines 35 may extend through the rear wall 126 of the upper housing 12 to outside the housing 10.

In some embodiments, the compressor 30 is a stationary high-efficiency low-noise compressor. The compressor 30 includes a motor 34 and a compression mechanism 36 driven by the motor 34. The compression mechanism 36 comprises the input end 31 and the output end 32. A plurality of buffer support feet 14 are arranged at bottom of the lower housing 11. The inner walls of the lower housing 11 and the upper housing 12 are provided with positioning structures 105. Each positioning structure 105 includes a recess, and a shock absorbing member 15 is secured in the recess of each positioning structure 105. Each absorbing member 15 is covered and fixed at a corresponding corner of the compressor 30 respectively in order to absorb shock generated by the compressor 30 in operation. Specifically, the motor of the compressor 30 includes a stator and a rotor rotatably mounted in the stator. The stator includes a plurality of laminations stacked together. The stator includes four corners. The four corners of the stator of the motor 34 are mounted to the four positioning structures 105 with four absorbing members 15 sandwiched between the corners and the positioning structures 105 respectively.

In this embodiment, the control panel 20 and the compressor 30 are both disposed in the accommodating cavity 102, the decorative panel 13 and the control panel 20 are located at opposite sides of the opening 104, the decorative panel 13 faces the control panel 20, the decorative panel 13 is parallel with the control panel 20, the digital display screen 21 and the touch switch 22 are visible from outside the housing 10 through the opening 104 and the decorative panel 13. In addition, a power switch 60 is disposed on the rear wall 126 of the upper housing 12, and the power switch 60 is electrically connected to the control panel 20. The inlet member 41 and the power switch 60 are disposed at the rear end of the housing 10 which is benefit to leave enough space to arrange the control panel 20, the decorative panel 13 and the outlet member 42 at the front end of the housing 10, and reduce the height of the housing 10. In some embodiments, the housing 10 has a length L in the lengthwise direction thereof and a height H in the height direction thereof, H/L<0.5. Preferably, H/L<0.4. In some embodiments, L=24.5 cm, H=9.5 cm. The housing 10 has a width W in the width direction thereof, W=15.5 cm.

The working process of this embodiment is described in detail as follows:

In use, when the power switch 60 is turned on and the touch switch 22 is touched to start the compressor 30, the gas-liquid mixture is sucked into the compressor 30 from the inlet member 41, and the gas-liquid mixture is dispersed and atomized in the compressor 30, and then output from the outlet member 42. During the process of atomization, the digital display screen 21 can display the use time countdown prompt, particle size adjustment and use time prompt for children and adults, the temperature and humidity of the atomization, etc., so that the atomization effect can be visualized.

FIG. 7 illustrates an atomizer according to another embodiment of the present application.

The main difference between the atomizer as shown in FIG. 7 and the atomizer as shown in FIGS. 1-5 is as following: in the atomizer as shown in FIG. 7, the input end 31 and the output end 32 of the compressor 30 both face the same side wall of the housing 10. That is, the axis of the input end 31 is perpendicular to that of the inlet member 41, and the axis of the output end 32 is perpendicular to that of the outlet member 42. Preferably, the cooling fan 50, the input end 31 and the output end 32 of the compressor 30 all face the same side wall of the housing 10. The input end 31, the output end 32 are parallel with the control panel 20, and the input end 31, the output end 32 and the cooling fan 50 are arranged towards a same side, such the atomizer can have a small and compact structure. The input end 31 and the output end 32 may be arranged in the lengthwise direction of the housing 10. Alternatively, the input end 31 and the output end 32 may be arranged in the height direction of the housing 10. That is, the input end 31 and the output end 32 are stacked or overlapped in the height direction of the housing 10. The working principle of the atomizer of this embodiment is similar to that of the atomizer described above.

As shown in FIG. 7, the motor 34 is arranged closer to the rear end of the housing 10, the compression mechanism 36 of the compressor 30 is arranged closer to the front end of the housing 10, and the cooling fan 50 is arranged beside the motor 34. As the compression mechanism 36 of the compressor 30 is arranged closer the front end of the housing 10, the connection pipe 71 may be shorter than the connection pipe 72. In one embodiment, a length ratio of the connection pipe 72 to the connection pipe 71 may be 1.5~3. For example, the length ratio may be 1.5, 2, 2.5, or 3.

By designing the control panel as an intelligent control panel, the control panel 20 has a digital display screen for displaying the working state of the atomizer, so as to realize the digital display function and bring convenience to use. At the same time, by cooperating with a cooling fan 50 and a cooling grille 101, the cooling effect of the compressor 30 is improved, and the compressor 30 is prevented from being overheated and damaged, thereby greatly extending the service life of the product. Orientations of the input end 31 and output end 32 of the compressor are perpendicular to the height direction of housing 10, which facilitates to reduce the height of the housing 10. The outlet member 42 is arranged at the front end of the housing 10 while the inlet member 41 is arranged at the rear end of the housing 20, which facilitates to arrange the intelligent control panel 20 and the decorative panel 13 at the front end of the housing 10.

The above are only the preferred embodiments of the present application, and are not intended to limit the present application. Therefore, any modification, equivalent replacement, improvement, etc. made to the above embodiments according to the technical practice of the present application still fall within the scope of the technical solution of the present application.

What is claimed is:

1. An atomizer with an intelligent control digital display function, comprising:
    a housing provided with an inlet member and an outlet member;
    a control panel arranged in the housing; and
    a compressor arranged in the housing and electrically connected with the control panel, the compressor comprising an input end in fluid communication with the inlet member and an output end in fluid communication with the outlet member;
    wherein the control panel is an intelligent control panel which comprises a digital display screen for displaying working state of the atomizer and a touch switch; and
    wherein the housing comprises a front end and a rear end in a lengthwise direction thereof, the front end of the housing is provided with an opening, the opening is covered with a decorative panel, the outlet member extends through the opening and the decorative panel, the control panel comprises a front face facing the decorative panel and a rear face facing the rear end of the housing, the decorative panel faces and covers the control panel with a gap formed therebetween in the lengthwise direction, and the digital display screen and the touch switch are mounted on the front face of the control panel and disposed in the gap and visible from outside of the housing through the opening and the decorative panel.

2. The atomizer with an intelligent control digital display function according to claim 1, wherein the touch switch is a capacitive touch switch which comprises a spiral spring with an axis perpendicular to the decorative panel and the control panel.

3. The atomizer with an intelligent control digital display function according to claim 1, wherein the housing comprises a lower housing and an upper housing, and the upper housing and the lower housing are engaged with each other to form an accommodating cavity therebetween, the control panel and the compressor are arranged in the accommodating cavity.

4. The atomizer with an intelligent control digital display function according to claim 3, wherein the outlet member and the inlet member are respectively arranged on the front and rear ends of the upper housing; or
    at least one cooling grille is located at a side wall of the upper housing.

5. The atomizer with an intelligent control digital display function according to claim 1, wherein the inlet member defines a first axis, and the outlet member defines a second axis which is substantially parallel with the first axis, the inlet member being disposed at the rear end of the housing, the outlet member being disposed at the front end of the housing.

6. The atomizer with an intelligent control digital display function according to claim 5, wherein orientations of the input end and output end of the compressor are substantially perpendicular to the lengthwise direction of the housing, and the lengthwise direction is substantially parallel with the first axis or the second axis; or
    the housing defines a height direction, orientations of the input end and output end of the compressor are substantially perpendicular to the height direction of the housing, and the height direction is substantially perpendicular to the first axis or the second axis.

7. The atomizer with an intelligent control digital display function according to claim 1, wherein the housing has a length L and a height H, H/L<0.5.

8. The atomizer with an intelligent control digital display function according to claim 1, wherein a handle extends forwardly from the housing such that the atomizer is portable, the inlet member defines a first axis, and the outlet member defines a second axis which is substantially parallel with the first axis, the handle extending from the housing in a direction parallel to the first axis and the second axis.

9. The atomizer with an intelligent control digital display function according to claim 8, wherein the housing comprises a lower housing and an upper housing engaged with the lower housing, the handle is C-shaped and comprises two parts extending forwardly from the upper housing and the lower housing respectively.

10. The atomizer with an intelligent control digital display function according to claim 1, wherein the housing comprises an upper housing, the opening is substantially D-shaped and defined in the upper housing, the decorative panel having a D-shaped configuration conformed to the D-shaped opening.

11. The atomizer with an intelligent control digital display function according to claim 1, wherein the control panel is parallel with the decorative panel; and
    the control panel and the decorative panel are respectively located at opposite sides of the opening; or
    the control panel is located in the housing, and the decorative panel is received in the opening.

12. The atomizer with an intelligent control digital display function according to claim 1, wherein the outlet member is exposed from the decorative panel, the control panel has an area less than that of the opening to allow the outlet member to pass through the opening, the outlet member and the control panel being arranged side by side in a width direction of the housing and being overlapped in a height direction of the housing.

13. The atomizer with an intelligent control digital display function according to claim 1, wherein the control panel comprises an outside side facing the decorative panel, and the touch switch and the display screen are mounted on the outside side of the control panel and face the decorative panel.

14. The atomizer with an intelligent control digital display function according to claim 1, wherein the housing comprises a lower housing and an upper housing engaged with the lower housing, the lower housing and the upper housing are provided with positioning structures, a shock absorbing member is secured in each of the positioning structures, and each absorbing member is covered and fixed at a corresponding corner of the compressor.

15. The atomizer with an intelligent control digital display function according to claim 1, wherein a plurality of buffer support feet is arranged at a bottom of the housing.

16. The atomizer with an intelligent control digital display function according to claim 1, wherein the housing is provided with a power switch, and the power switch is electrically connected with the control panel.

17. The atomizer with an intelligent control digital display function according to claim 1, wherein the input end and the output end of the compressor face a same side wall of the housing; or the input end and the output end of the compressor face two opposite side walls of the housing, respectively.

18. The atomizer with an intelligent control digital display function according to claim 1, wherein the housing is provided with a cooling grille, and the compressor has an output shaft, a cooling fan is arranged on the output shaft and faces the cooling grille, and the cooling fan, the input end and the output end of the compressor face a same side wall of the housing.

19. The atomizer with an intelligent control digital display function according to claim 1, wherein the input end of the compressor is connected to the inlet member via a connection pipe; or the output end of the compressor is connected to the outlet member via another connection pipe.

20. The atomizer with an intelligent control digital display function according to claim 1, wherein the decorative panel is translucent.

\* \* \* \* \*